United States Patent [19]

Euteneuer

[11] Patent Number: 5,681,345
[45] Date of Patent: Oct. 28, 1997

[54] SLEEVE CARRYING STENT

[75] Inventor: Charles L. Euteneuer, Sts. Michael, Minn.

[73] Assignee: Scimed Life Systems, Inc., Maple Grove, Minn.

[21] Appl. No.: 773,610

[22] Filed: Dec. 30, 1996

Related U.S. Application Data

[63] Continuation of Ser. No. 396,639, Mar. 1, 1995, abandoned.

[51] Int. Cl.$^6$ .................................................. A61M 29/00
[52] U.S. Cl. ............................ 606/198; 606/194; 623/1; 623/12
[58] Field of Search ........................ 623/1, 12; 606/191, 606/192, 194, 195, 198

[56] References Cited

U.S. PATENT DOCUMENTS

| | | | |
|---|---|---|---|
| 4,485,096 | 11/1984 | Bell | 424/532 |
| 4,485,097 | 11/1984 | Bell | 424/549 |
| 4,539,716 | 9/1985 | Bell | 623/1 |
| 4,546,500 | 10/1985 | Bell | 435/1.1 |
| 4,604,346 | 8/1986 | Bell et al. | 606/132 |
| 4,837,379 | 6/1989 | Weinberg | 424/548 |
| 4,986,831 | 1/1991 | King et al. | 623/1 |
| 5,100,429 | 3/1992 | Sinofsky et al. | 606/195 |
| 5,106,949 | 4/1992 | Kemp et al. | 530/356 |
| 5,151,105 | 9/1992 | Kwan-Gett | 623/1 |
| 5,192,311 | 3/1993 | King et al. | 623/1 |
| 5,195,984 | 3/1993 | Schatz | 606/195 |
| 5,207,705 | 5/1993 | Trudell et al. | 623/1 |
| 5,236,447 | 8/1993 | Kubo et al. | 623/1 |

*Primary Examiner*—Michael Buiz
*Assistant Examiner*—Patrick W. Rasche
*Attorney, Agent, or Firm*—Vidas, Arrett & Steinkraus

[57] ABSTRACT

A sleeve carrying stent for implantation within a body lumen comprising a radially expandable cylindrical stent component having an inner wall and an outer wall, a plurality of elongated support struts, and a sleeve secured to the ends of the struts, wherein the struts are preferably parallel and may be loosely interlocked with the stent component, and wherein the stent component is able to move longitudinally independent of the struts.

40 Claims, 8 Drawing Sheets

SLEEVE CARRYING STENT

This is a continuation of application Ser. No. 08/396,639 filed on Mar. 1, 1995 now abandoned.

FIELD OF THE INVENTION

This invention relates to a sleeve carrying stent which can be surgically implanted inside of blood vessels or other related lumen, and more particularly a conventional stent adapted to carry a luminal collagen sleeve to a targeted area in an improved manner.

BACKGROUND OF THE INVENTION

Vascular disease in man has become one of the primary causes of overall poor health and death in recent years. Vascular diseases occur throughout the body and affect the heart, limbs, and other parts of the body. Arterial disease has caused death by heart attack, reduced physical activity due to constriction or blockage of vessels or arteries serving the muscles of the heart, and constriction or blockage of vessels and arteries to the limbs. These vascular diseases have resulted in the loss of extremities, wherein the blood flow becomes sufficiently restricted to prevent proper nourishment of the tissue of the extremities, and have caused death when reduced blood flow to the muscles of the heart starve the heart of needed blood.

Certain treatments for arterial diseases depend upon protheses or vascular transplants for the purposes of returning proper levels of blood flow to affected parts of the body. A variety of techniques an protheses have been tried in an effort to provide a surgically applied prosthesis capable of restoring proper blood flow to the afflicted part of the body while at the same time repairing the injured or affected part of the targeted area. Modern synthetic fabric technology has provided prosthese such as collagen sleeves which have been used as a substitute for diseased arteries and vessels. Successful grafting of such fabric replacement prostheses requires that coagulase tissue generated by the body become implanted in the fabric prosthesis in order to ensure a successful long-term graft. Tissue equivalents prepared from a hydrated collagen lattice contracted by a contractile agent, such as fiberblast cells or blood platelets to form the tissue equivalent are disclosed in U.S. Pat. Nos. 4,485,096; 4,485,097; 4,539,716; 4,546,500; and 4,604,346. These tissue equivalents include, but are not limited to, equivalents of epithelious tissue, connective tissue, cartilage, bone, blood, organs, glands and blood vessels and comprise living cells and extra cellular matrix molecules, principally collagen, and may optionally be provided with components now typically found in normal tissue.

The use of prostheses for the replacement of blood vessels and other anatomical ducts is of great interest in medicine and veterinary work. To be acceptable in a given application the prosthesis must exhibit the proper mechanical properties and bio-acceptable composition for the given application. For example, vascular prostheses must provide a bio-acceptable surface which is conducive to cellular attachment and sustained blood flow, yet is strong enough not to split or tear. It is critical that the vascular prosthesis not tear along the body of the prosthesis or at the site of the sutures.

Collagen is an example of a bio-material which has many properties desirable of medical prosthesis. The advantage of using collagen in such devices is that collagen occurs naturally in the human body, and the graft or protheses eventually absorbed into the tissue to which is it attached. Collagen is usually found in the principal protein component of the extra-cellular matrix. In mammals, collagen sometimes constitutes as much as 60% of the total body protein. It comprises most of the organic matter of skin, tendons, bones, teeth, and occurs as fibrous inclusions in most of the body structure. Collagen is a natural substance for cell adhesion and is the major tensile load-bearing component of the muscular-skeletal system. Collagen also has application in the manufacture of implantable prostheses and the preparation of living tissue equivalents.

Luminal collagen sleeves can be combined with conventional luminal stents to repair and support damaged bodily vessels. The collagen sleeve incorporates a non-thrombogenic surface and promotes growth of endothelial cells, and can be used as a reservoir or point of attachment for therapeutic agents. As the sleeve carrying stent expands to support the targeted lumen, the collagen sleeve comes in contact with the inner surface of the luminal wall. The contact allows cellular growth between the wall of the lumen and the collagen sleeve forming a bio-compatible vascular prosthesis. In time, the sleeve and stent are incorporated into the wall of the lumen, reinforcing and sealing the vessel, and allowing for normal blood flow and bodily acceptability.

Stents are normally used in situations where part of the vessel wall or stenotic plaque blocks or occludes blood flow in the vessel. Normally a balloon catheter is utilized in a percutaneous transluminal coronary angioplasty (PTCA) procedure to enlarge the occluded portion of the vessel. However, the dilation of the occlusion can form flaps, fissures and dissections which threaten reclosure of the dilated vessel or even perforations in the vessel wall. Implantation of stents can provide support for such problems and prevent reclosure of the vessel or provide patch repair for a perforated vessel. The stent overcomes the natural tendency of the vessel walls of some patients to collapse, thereby maintaining a more normal flow of blood through that vessel than would be possible if the stent were not in place. When the stent is positioned across the lesion, it is expanded, causing the length of the tube to decrease and the diameter to expand. Depending on the materials used in construction of the stent, the tube maintains the new shape either through mechanical force or otherwise.

A problem that arises in using a conventional stent as a carrier for a sleeve is the effect that the shortening of the stent during expansion has on the sleeve itself. Sleeves are usually either sutured onto the stent or are in direct contact with the stent. As the stent radially expands after being located in the target area it shortens in length, thus shortening the sleeve or even actually tearing it because of the abrasive forces of the stent on the sleeve. This creates a vascular prosthesis with undesirable wrinkles and possible tears. This effect on the luminal sleeve decreases the surface area which the sleeve was initially able and intended to cover, and hinders the ability to predict the actual spanning or placement of the sleeve. The wrinkles that result from the shortening of the stent also have a negative effect on the blood flow itself. When the stent is permanently placed in a vessel, the continuous stress from the flow of the fluid along the wrinkles within the vessel could cause internal turbulence hindering normal blood flow.

It is desirable that replacements for vessels and arteries are uniform in thickness, because thin portions of the wall may be susceptible to rupture. The human body tends to compensate for weaknesses in the walls of blood vessels and it has been proposed that the unevenness will be compensated by tissue growth in the weaker areas so that the interior surface of such a tube will become uneven when the body attempts to compensate for weaknesses in the tube wall at thin portions or nicks. This, of course, produces a less than desirable final result since a smooth shiny uniform interior wall is desired in the transplanted graft. Wrinkles would tend to cause the same problem. During the period of growth of the endothelial cells which contribute in the incorporation of the sleeve into the tissue, the wrinkles can cause uneven growth of tissue thus compounding the problem of smooth blood flow through the sleeve.

The movement of the stent during expansion also can create abrasive forces on sleeves that are not sutured onto the stent itself, but are in direct contact with the stent causing possible tearing. It is preferable to have a luminal sleeve delivery device which maintains the length of the sleeve to create a smooth application between the original vessel and the vascular prosthesis, and to have a device in which the stent moves independent of the sleeve preventing it from rubbing the sleeve or tearing it during expansion. The longitudinal abrasion on the wall of the sleeve from the shortening of the stent and the unpredictable coverage when fully in place complicate the insertion of the vascular prosthesis.

U.S. Pat. No. 5,236,447 discloses an artificial tubular organ composed of a tubular supporting frame made of a plastic material which is provided on at least one surface a medical prosthetic material that comes in direct contact with the frame and lacks independent movement. The frame is composed of a plurality of rings arranged on an axis, and a plurality of connecting portions extending between adjacent rings so as to connect them to each other forming a cylindrical structure. The medical prosthetic material may be a woven fabric, a knitted fabric, a nonwoven fabric, or a combination thereof. Preferred fabric includes absorbable macromolecular yarns and nonabsorbable macromolecular yarns. This device is used as an artificial tubular organ for use in substitution or reconstruction of tubular organs such as blood vessels, tracheae and esophagi. The structure disclosed is a rigid, noncollapsible structure making it difficult to insert in cumbersome target areas.

U.S. Pat. No. 4,986,831 describes a homo graft composed of collagenous tissue generated on a prosthetic device. A cylindrical substrate is suspended by an anchoring device in the lumen of a blood vessel allowing blood to flow over the inside as well as the outside surfaces. One of the surfaces of the substrate is a thrombogenic surface or supports a thrombogenic mesh material to promote growth of a tube of collagenous tissue suitable for use as a surgical graft. The body generates collagenous growth on the surface of the substrate while the substrate is freely suspended in the vessel. The substrate is not intended to remain in a particular location. Therefore is not expandable and is removed from the vessel after which a tubular homograft of collagenous tissue is removed from the substrate to be used in some other location as graft material.

U.S. Pat. No. 5,151,105 discloses a collapsible vessel sleeve for implanting inside a live tissue fluid vessel and system. The sleeve is directly connected to or in direct contact with a collapsible circular stent to support the sleeve. A pair of linear stiffeners are each sutured or otherwise loosely attached to opposite sleeve exterior sides to maintain the length of the sleeve. The collapsibility is accomplished by (1) initially skewing the tubular graft toward its trailing end, and (2) compressing the circular stents inwardly toward the catheter at the locations adjacent the end points of connection of the longitudinal stiffeners to the tubular body portion. Positioning wires are twisted onto and thus removably attached to the stent at diametrically opposing points of attachment about the cylindrical body portion. A capsule band is wound around the sleeve and stent to maintain the collapsed sleeve for travel to the target area, and is maneuvered into place by means of the catheter and the guide wires. When the device is in the targeted area the sleeve/stent is released and is urged into place by the guide wires. Manipulation is required to precisely position and fully expand the graft within the damaged lumen. The surgeon needs to slightly agitate or reciprocate the positioning wires to make the circular stents adopt positions in planes normal to the axis of the vessel. When in place, the surgeon detaches the positioning wires and removes the catheter device. A tacking system can be used in order to secure the sleeve in the targeted lumen area.

Difficulties have been encountered in the placement of sleeves into targeted damaged vessels via a carrying stent. There is a need for a sleeve carrying device that resists wrinkling or tears of the sleeve during expansion of the stent, for a sleeve carrying stent in which the stent moves independent from the sleeve to ensure accurate placement, and is easy to insert into a predetermined target area.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

SUMMARY OF THE INVENTION

This invention relates to a novel sleeve carrying stent as well as an improved way to incorporate biocompatible sleeves into damaged vessels. More specifically it improves the installation of a luminal sleeve while stabilizing the vessel via the expandable stent. This device allows a stent, accompanied by a sleeve, preferably made of collagen, to be placed in the target area, maintaining tension and support of the sleeve while the stent shortens during radial expansion.

The sleeve carrying stent is for implantation within a body lumen and comprises a radially expandable cylindrical stent component having an inner wall and an outer wall, a plurality of elongated support struts, and a sleeve secured to the ends of the struts, wherein the struts are preferably parallel and may be loosely interlocked with the stent component, and wherein the stent component is able to move longitudinally independent of the struts.

It is an object of the present invention to provide an implantable luminal sleeve that does not require major abdominal surgery in order to effect implantation.

It is still another object to provide an implantable sleeve that will maintain itself in a stable position after placement in a patient.

It is another object of the invention to allow stent expansion without altering the position or structural integrity of the sleeve.

It is a further object of the present invention to provide a sleeve carrying stent capable of being implanted simply and reliably.

Other objects, features, and characteristics of the present invention, as well as the methods of operation and functions of the related elements of the structure, and the combination of parts and economics of manufacture, will become more apparent upon consideration of the following description with reference to the accompanying drawings, all of which form a part of this specification.

DETAILED DESCRIPTION OF THE INVENTION

Figure 1:
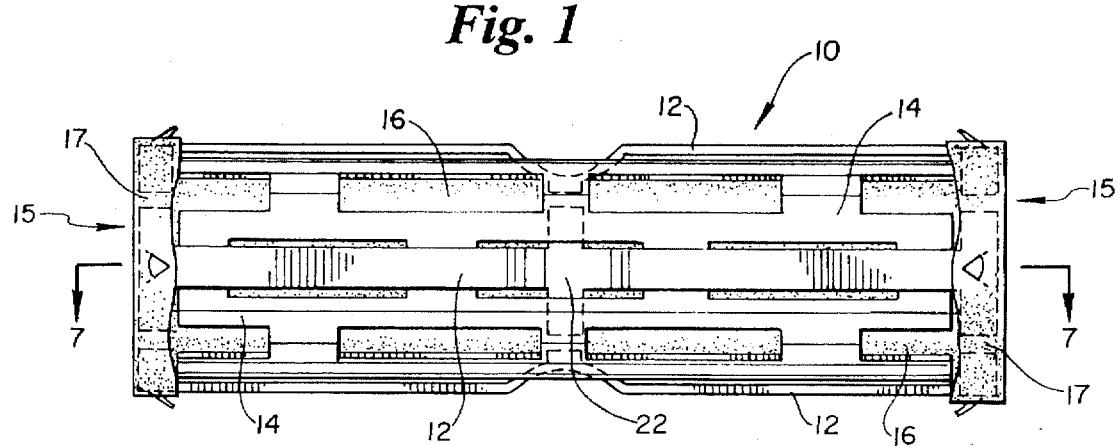
FIG. 1 shows a side elevational view of the invention.

Referring to the drawings, FIG. 1 illustrates the fully assembled sleeve carrying stent, generally designated 10. The device is composed of a plurality of elongated struts 12 loosely connected to a conventional stent apparatus, generally designated 14. The struts 12 are positioned in a parallel fashion in a radially spaced manner around the body of the stent. The structure further comprises a luminal sleeve, preferably a collagen sleeve, generally designated 16, positioned on the opposite side of the stent wall as that of the struts 12. The ends 17 of the sleeve 16 are folded over the outside of the stent open ends 15 and are firmly attached to the ends of the struts 12.

Figure 2:
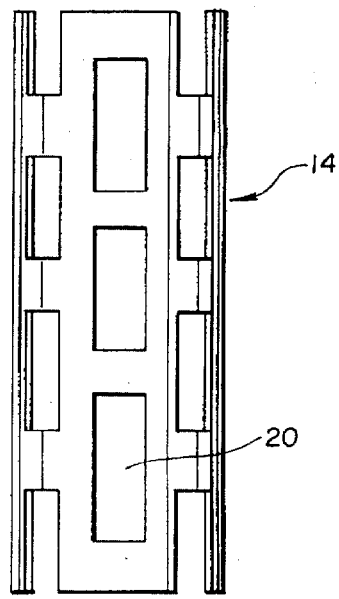
FIG. 2 shows a side elevational view of a conventional unexpanded stent.

FIG. 2 illustrates a conventional stent 14 that can be used in the present invention. Stents that can be utilized in the preferred embodiment should have some kind of openings or slots 20 along the body of the stent to facilitate the loose interlocking mechanism 22 between the struts 12 and the stent 14. The stent in FIG. 2 demonstrates an acceptable conventional stent due to its multiple slots 20 incorporated in the wall of the stent. A conventional stent usually is cylindrical in shape having open ends, an inner wall and an outer wall. The present invention can utilize a variety of conventional scents that are radially expandable, whether self-expandable or expanded by some means. Typically, a balloon is used for expansion.

Figure 6:
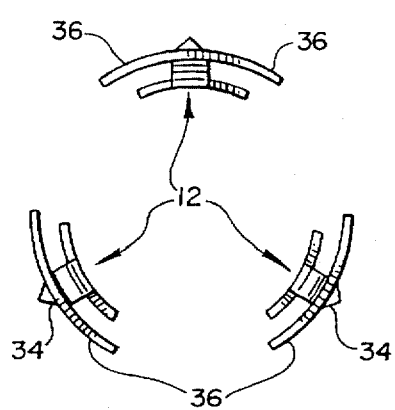
FIG. 6 shows a front elevational view of the configuration of the struts when assembled as shown in FIG. 1.
Figure 5:
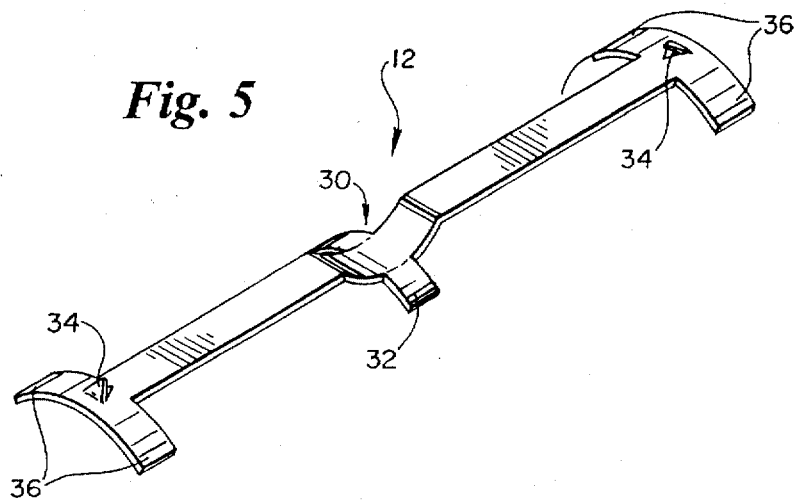
FIG. 5 shows a perspective view of a strut.
Figure 3:
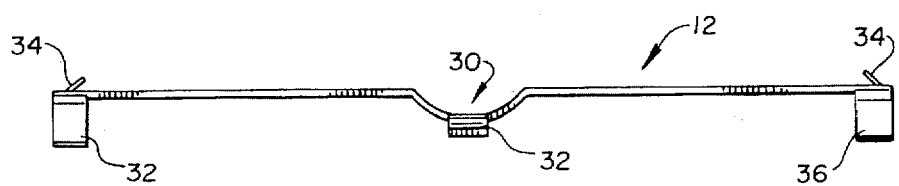
FIG. 3 shows a side elevational view of a strut.
Figure 4:
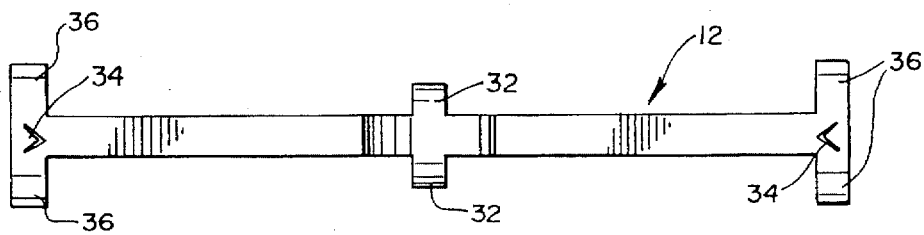
FIG. 4 shows a top elevational view of a strut.

FIGS. 3–6 illustrate a preferred structure of the struts 12. The middle of a strut forms a depression 30 or a slight dip to allow for the interlocking mechanism 22 with the slots 20 of the stent 14. Two tabs 32 protrude perpendicularly from the depressed area 30 and are utilized in the interlocking mechanism preventing the struts 12 from separating from the stent 14. Barbs 34 are located on the surface of the struts 12 at both ends and are used to secure the ends of the luminal sleeve 17 to maintain tension of the sleeve 16. In the most preferred embodiment there are three struts and the ends of the struts further comprise rounded radial perpendicular members 36 that enhance the cylindrical nature of the device as demonstrated in FIG. 6 and aid in guiding the luminal sleeve 16 over the ends of the struts 12 to be secured by the barbs 34. The struts are arranged around the wall of the stent in a equidistant radially spaced fashion as shown in FIG. 6.

The luminal sleeve 16 is cylindrical in shape and can be made from a variety of biocompatible material, depending upon the intended use. A luminal collagen sleeve is an example of such possibilities and is the focus of this invention. Other sleeve compositions may include polytetrafluoroethylene, polyesters, such as dacron®, polyurethanes and silicones.

Figure 7:
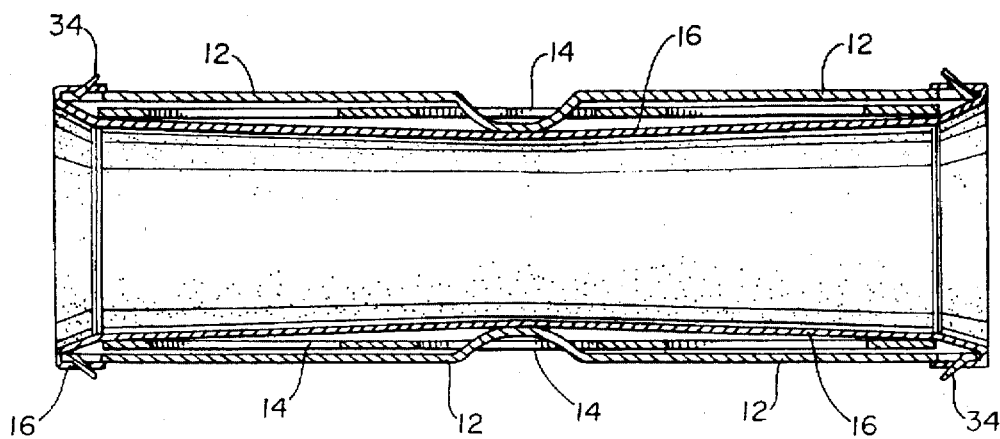
FIG. 7 shows a sectional view along the line 7—7 in FIG. 1.

The sleeve in one particular embodiment is positioned inside of the stent 14 with the ends 17 of the sleeve 16 extending out toward the ends of the stent, folded over the ends of the struts and secured by the barbs 34 as shown in the sectional view of FIG. 7. The collagen sleeve 16 is not connected at all to the stent, allowing the stent 14 to move independently between sleeve 16 and the struts 12, the stent and the struts being loosely interlocked near the center of the stent.

Figure 12:
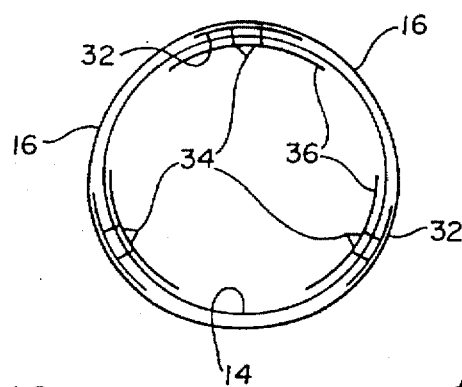
FIG. 12 shows a mechanical schematic diagram of a particular embodiment of the invention.
Figure 13:
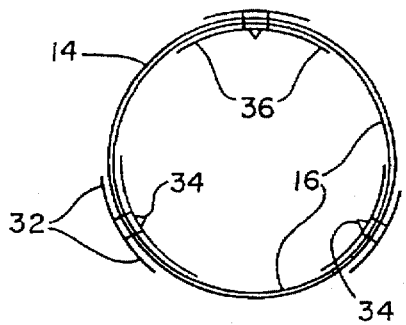
FIG. 13 shows a mechanical schematic diagram of a particular embodiment of the invention.
Figure 14:
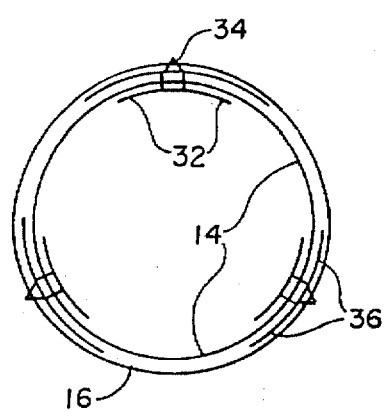
FIG. 14 shows a mechanical schematic diagram of a particular embodiment of the invention.

In an alternative embodiment the struts would be positioned on the inside of the stent wall and the sleeve would be positioned on the outside of the stent wall or totally around the stent as illustrated by the mechanical schematic diagram of FIG. 12, which shows an end spatial relationship view of the embodiment. Still another embodiment would be one in which the struts and the sleeve are positioned on the same side of the stent wall, maintaining the floating interlocking mechanism between the struts and the stent as illustrated by the mechanical schematic diagram of 13 and 14, which show end spatial relationship views of the embodiment. The positioning of the particular parts is generally not important, as long as the sleeve is secured by the struts to maintain tension and to prevent shortening of the sleeve, and the stent is allowed longitudinal independent movement.

Figure 15:
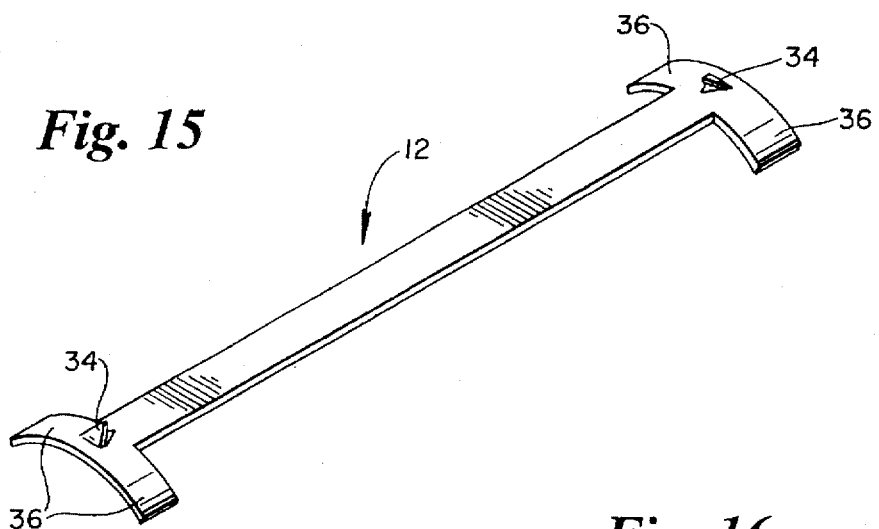
FIG. 15 shows a perspective view of a strut as in FIG. 5 without the interlocking mechanism.
Figure 16:
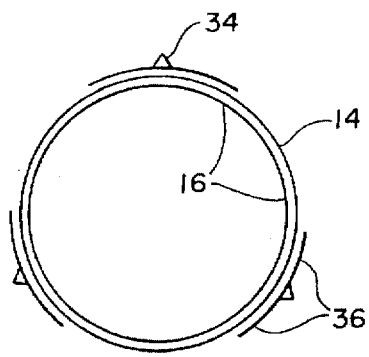
FIG. 16 shows a mechanical schematic diagram of a particular embodiment of the invention.
Figure 17:
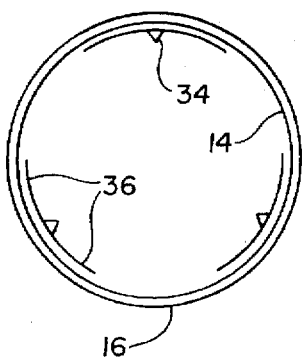
FIG. 17 shows a mechanical schematic diagram of a particular embodiment of the invention.

The configurations mentioned above may also be made without the interlocking mechanism between the struts and the stent 22. In this case the struts 12 do not have the depression 30 or tabs 32, as shown in FIG. 15. The arrangement of the sleeve and the struts are such that the stent is sandwiched and thus held substantially in place throughout the procedure. FIGS. 16 and 17 illustrate this particular embodiment by showing spatial relationship end views. FIG. 16 shows an embodiment of the invention wherein the struts are on the outside of the stent wall and the sleeve is on the inside. FIG. 17 shows an embodiment of the invention having the opposite configuration.

Figure 18:
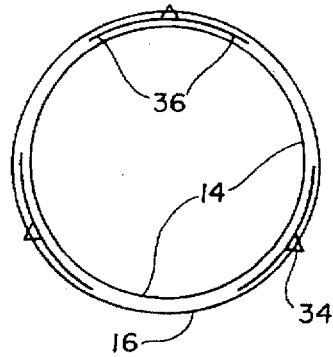
FIG. 18 shows a mechanical schematic diagram of a particular embodiment of the invention.
Figure 19:
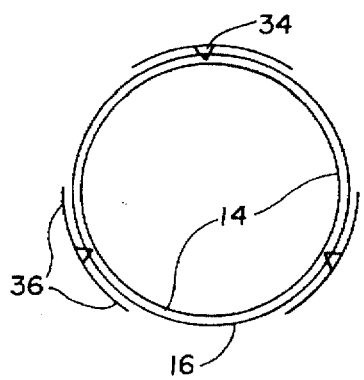
FIG. 19 shows a mechanical schematic diagram of a particular embodiment of the invention.

FIGS. 18 and 19 demonstrate the configuration of still another embodiment, wherein the sleeve and the struts are on the same side, the outside, of the stent wall and there is no interlocking mechanism. The sleeve and struts are carried by stent to the target area. As the stent radially expands and shortens, the sleeve also radially expands, but stays constant in terms of length.

Figure 20:
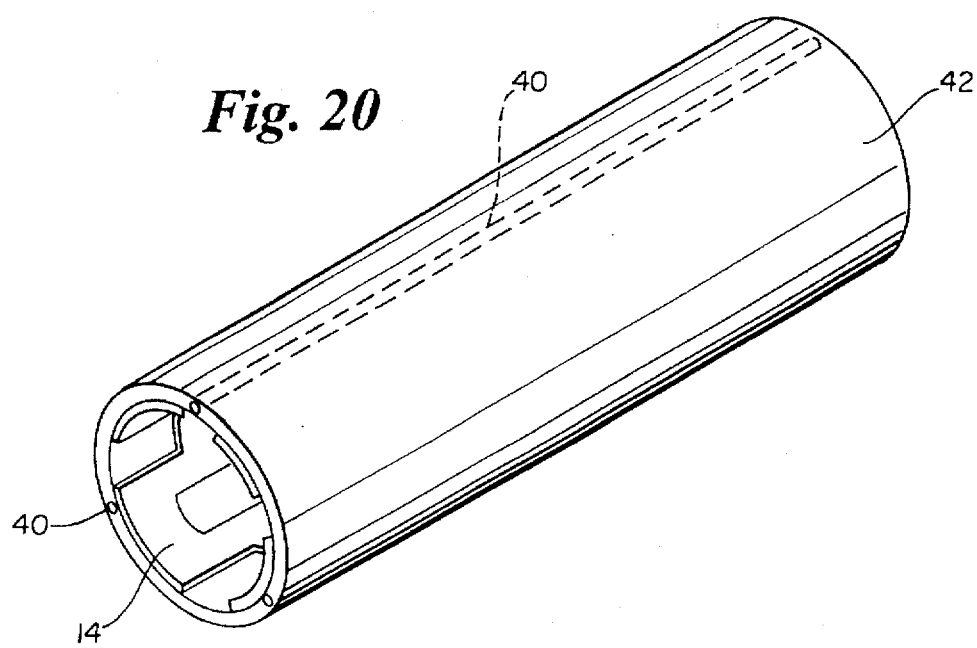
FIG. 20 shows a perspective view of a particular embodiment of the present invention.
Figure 21:
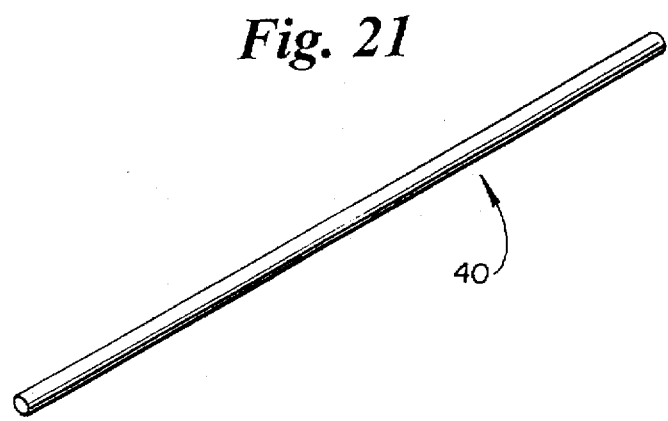
FIG. 21 shows a rod-shaped strut which is used in the embodiment shown in FIG. 20.
Figure 22:
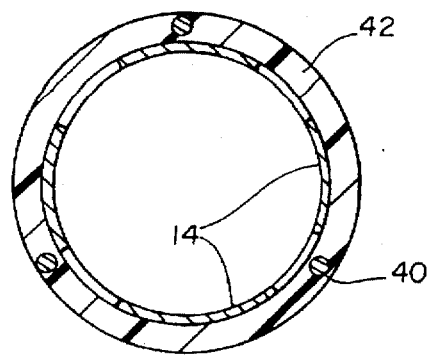
FIG. 22 shows a front elevational view of the embodiment shown in FIG. 20.

Another embodiment is illustrated by FIGS. 20–22. In this embodiment the struts are rod-shaped 40 and are incorporated in the sleeve 42, the sleeve being created to have adequate thickness to enclose the rod-shaped struts. The stent 14 is positioned inside the sleeve/struts combination as shown in the perspective view of FIG. 20 and the spatial relationship end view of FIG. 22.

Figure 23:
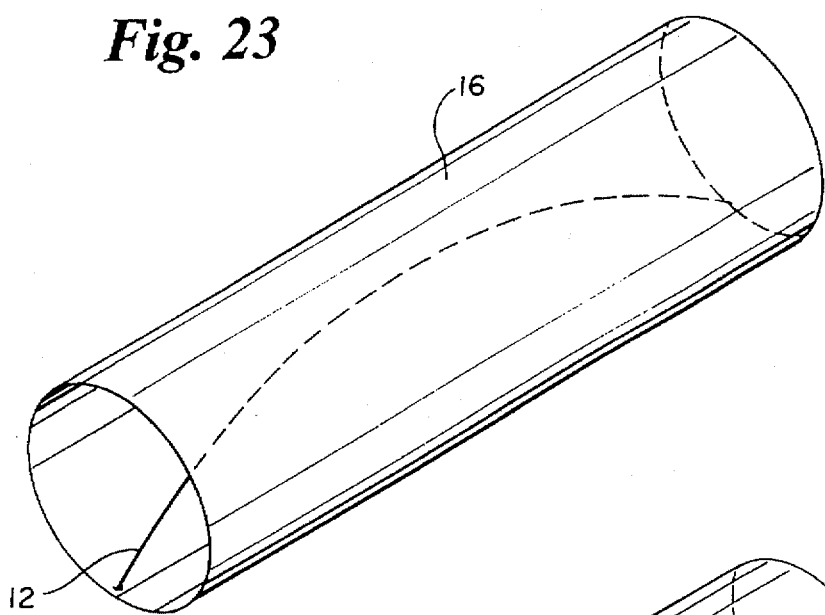
FIG. 23 mechanical schematic diagram showing the positioning of a strut and the sleeve an alternative embodiment of the invention.
Figure 24:
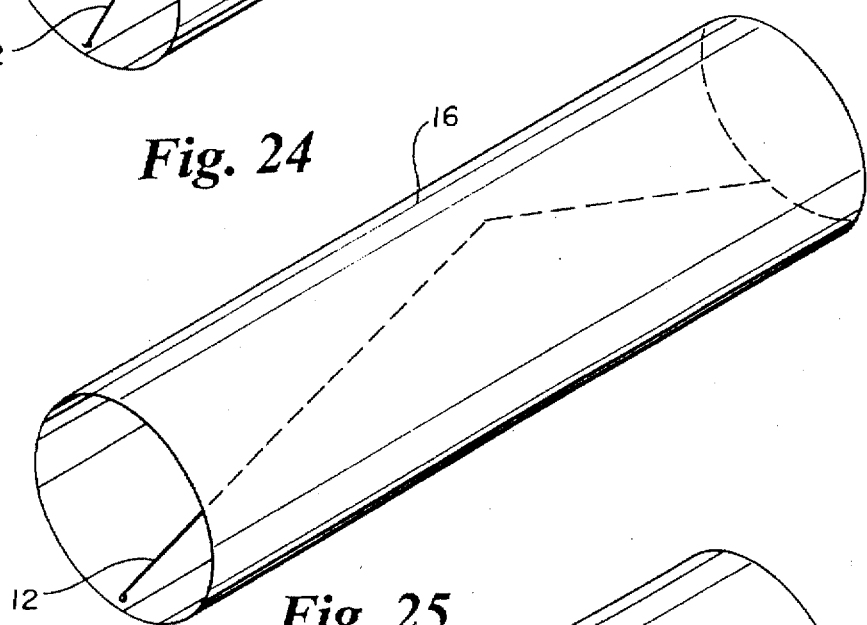
FIG. 24 mechanical schematic diagram showing the positioning of a strut and the sleeve an alternative embodiment of the invention.
Figure 25:
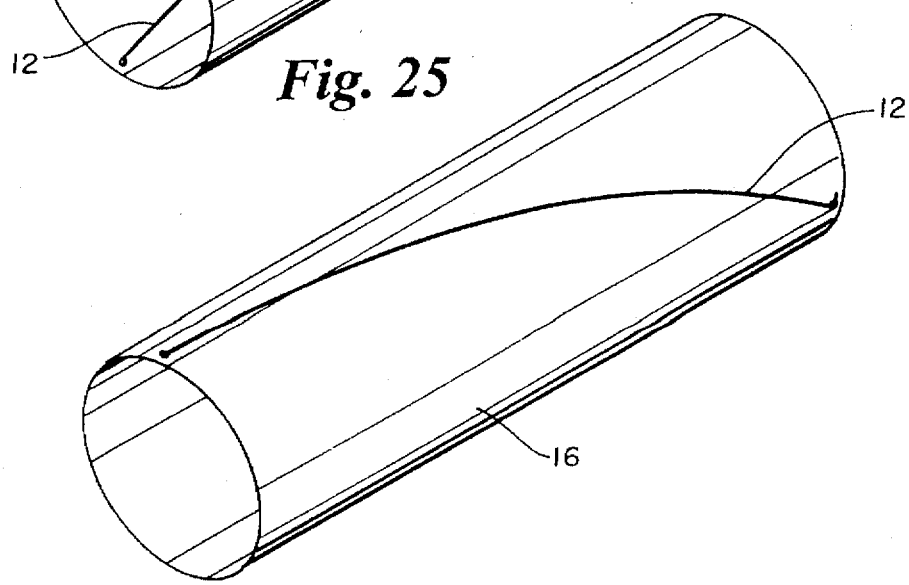
FIG. 25 mechanical schematic diagram showing the positioning of a strut and the sleeve an alternative embodiment of the invention.
Figure 26:
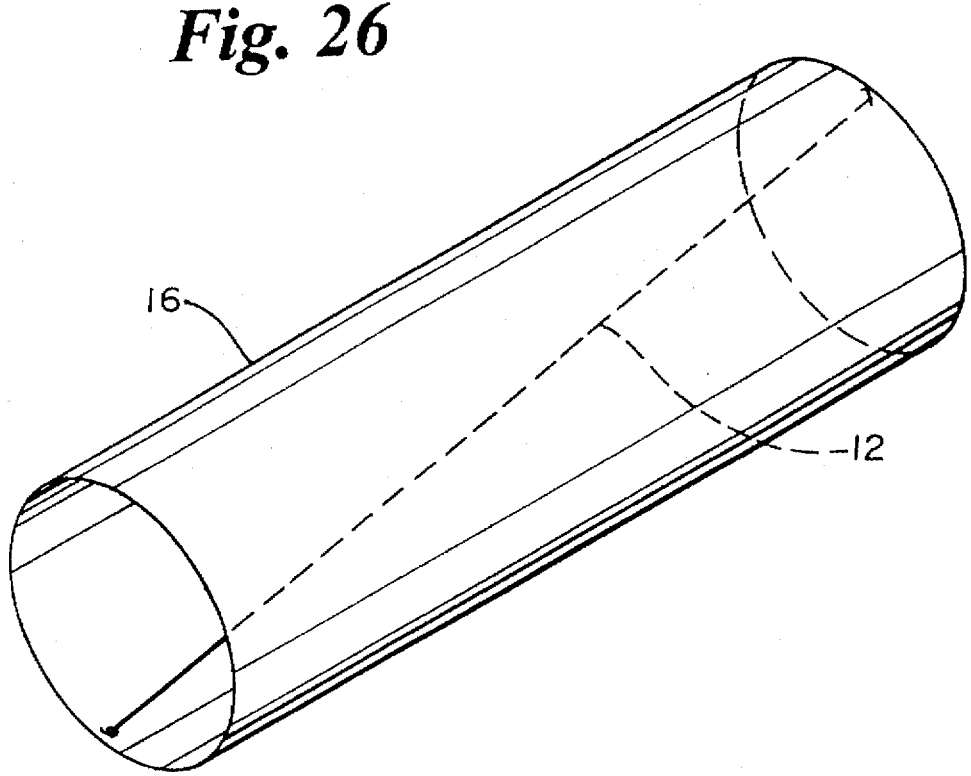
FIG. 26 is a mechanical schematic diagram showing the positioning of a strut and the sleeve in an alternative embodiment of the invention.
Figure 27:
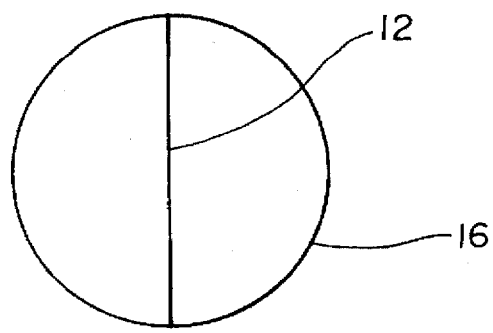
FIG. 27 is an end view of FIG. 26.

In the present invention it is not required that the struts be parallel nor straight. The struts may be curved as shown in FIG. 23, angled to form an apex as shown in FIG. 24, angled across the body of the stent either on the inside or the outside of the sleeve as shown in FIG. 25 or they may be diagonally positioned on the inside of the stent wall from one end to the other as shown in FIGS. 26 & 27. The basic functional requirement is that the struts urge the sleeve longitudinally outward.

The importance of the present invention is the independent movement of the stent without adversely affecting the sleeve and the maintaining of tension and support of the sleeve. The exact positioning of the parts is dictated by the purpose for which the device is to be used.

Figure 8:
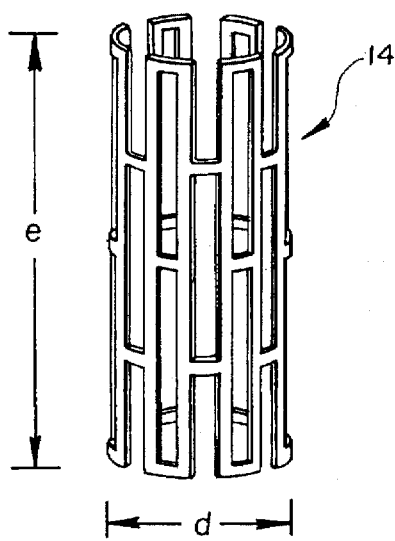
FIG. 8 shows a perspective view of a collapsed conventional stent.
Figure 9:
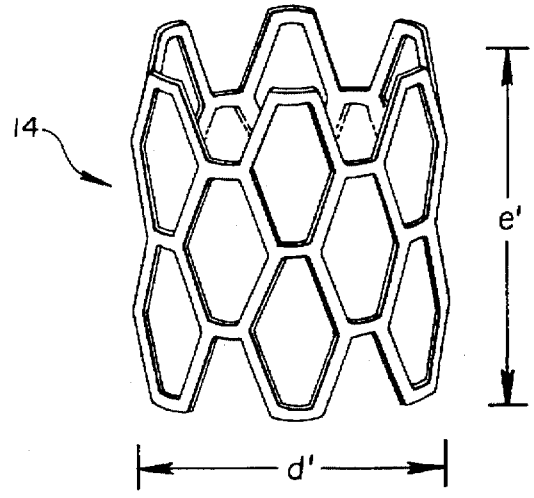
FIG. 9 shows a perspective view of an expanded conventional stent.

The conventional carrier stent 14 can be collapsed as shown in FIG. 8 enabling it to be inserted into the targeted area by way of an insertion device such as a catheter. In the collapsed state, the stent has a diameter of d and a length of e. After being positioned in the target lumen the stent may be expanded via balloon catheter or self-expansion as shown in FIG. 9, changing the stent in length and diameter urging the collagen sleeve against the vessel wall. In its expanded form the stent has a diameter d' and a length e'. This change in length is the focus of the problem in prior collagen carrying stents. As the stent expands it shortens in length and thus wrinkling the sleeve or even tearing the sleeve due to the abrasive forces. In the present invention the stent is able to move independent of the sleeve preventing it from affecting the tension in the sleeve.

Figure 10:
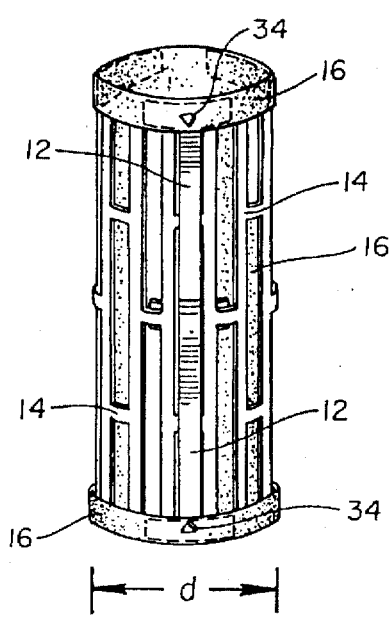
FIG. 10 shows a perspective view of an assembled collapsed sleeve carrying stent.
Figure 11:
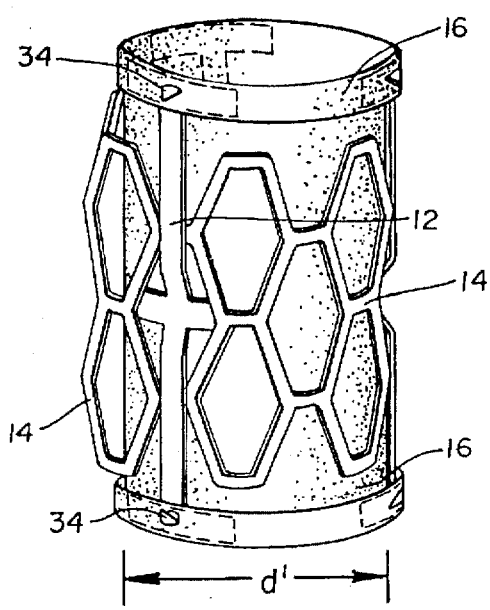
FIG. 11 shows a perspective view of an assembled expanded sleeve carrying stent.

FIGS. 10 and 11 illustrate the expansion of the stent 14 with the sleeve 16 and the struts 12 incorporated. FIG. 10 shows a collapsed stent having length e and a diameter d with three struts interlocked 22 to the outside of the stent 14, and with a sleeve 16 positioned on the inside of the stent 14. The ends of the sleeve are folded over the ends of the struts and secured by the barbs on the ends of the struts. As the stent radially expands to diameter d' and its length shortens to e' as shown in FIG. 11 the length of the sleeve 16 remains constant and the struts 14 maintain constant tension on the sleeve. The stent 14 moves independent of the struts and the sleeve, preventing the movement of the stent 14 from adversely affecting the sleeve 16. The struts move out radially with stent, but do not shorten, maintaining tension and support of the sleeve.

As shown, these luminal collagen sleeves can be combined with conventional luminal stents to repair and support damaged bodily vessels. The collagen sleeve incorporates a non-thrombogenic surface and promotes growth of endothelial cells, and can be used as a reservoir or point of attachment for therapeutic agents. As the sleeve carrying stent expands to support the targeted lumen, the collagen sleeve comes in contact with the inner surface of the luminal wall. The contact allows cellular growth between the wall of the lumen and the collagen sleeve forming a bio-compatible vascular prosthesis. In time, the sleeve and stent are incorporated into the wall of the lumen reinforcing and sealing the vessel, allowing for normal blood flow and bodily acceptability.

Essentially the present invention is a vascular prosthesis of improved biocompatability. The improvement is in the delivery of the sleeve. The present design allows the sleeve to be delivered fully extended without any wrinkles in the sleeve due to the shortening of conventional carrier stents. The present invention allows for uniform growth and smooth blood flow through the device. The struts maintain the length of the sleeve enabling the prosthetic device to fully span the targeted problem area. This enables the user to take advantage of the entire length of the collagen sleeve, allowing location of the sleeve in a more predictable manner.

The above disclosure is intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A sleeve carrying stent for implantation within a body lumen comprising in combination:

a radially expandable cylindrical stent component having open ends, an inner wall and an outer wall;

a plurality of elongated support struts, each of said plurality of struts having a first end and a second end, said struts being carried by the stent component, wherein the stent component is able to move longitudinally independent of the struts; and a biocompatible open ended tubular sleeve associated with the stent component, wherein the sleeve is positioned parallel with the stent component and is secured to the struts; said sleeve carrying stent being constructed and arranged for implantation and expansion with the sleeve and struts incorporated with the stent.

2. A sleeve carrying stent as in claim 1 wherein the struts are parallel with the stent component, the sleeve has a first end and a second end, and the composition of the sleeve is chosen from a group consisting of collagen, polytetrafluoroethylene, polyesters, polyurethane and silicones.

3. A sleeve carrying stent as in claim 2 wherein the struts have a longitudinal axis and further are loosely interlocked with the stent component.

4. A sleeve carrying stent as in claim 3 wherein the struts are loosely interlocked to the stent component at a point generally equidistant from either end of the stent component.

5. A sleeve carrying stent as in claim 4 wherein the struts have securing means, the ends of the sleeve being secured in placed by the securing means, and wherein the length of the struts and the sleeve remain substantially constant during the radial expansion of the stent component.

6. A sleeve carrying stent as in claim 5 wherein the struts are radially spaced and have substantially the same length as the stent component in its collapsed form.

7. A sleeve carrying stent as in claim 6 wherein there are three struts.

8. A sleeve carrying stent as in claim 7 wherein the struts have radial perpendicular members extending from the ends of the struts, the members having a rounded configuration around the longitudinal axis of the strut.

9. A sleeve carrying stent as in claim 8 wherein the struts and the sleeve are on the same side of the stent wall.

10. A sleeve carrying stent as in claim 2 wherein the struts have securing means, the ends of the sleeve being secured in placed by the securing means, and wherein the length of the struts and the sleeve remain substantially constant during the radial expansion of the stent component.

11. A sleeve carrying stent as in claim 10 wherein the struts are radially spaced and have substantially the same length as the stent component in its collapsed form.

12. A sleeve carrying stent as in claim 10 wherein there are three struts.

13. A sleeve carrying stent as in claim 12 wherein the struts have radial perpendicular members extending from the ends of the struts, the members having a rounded configuration around the longitudinal axis of the strut.

14. A sleeve carrying stent for implantation within a body lumen comprising:

a radially expandable cylindrical stent component having open ends an inner wall and an outer wall:

a plurality of elongated support struts carried by the stent component parallel thereto, the struts being loosely interlocked with the stent component, each of said plurality of struts having a first end, a second end, a longitudinal axis, a central portion, a depression, and tabs positioned approximately at the central portion of the struts and on the opposite side of the stent wall than that of the longitudinal axis of the struts, said tabs projecting perpendicularly from the depression, wherein the stent component is able to move longitudinally independent of the struts; and a biocompatible open ended tubular sleeve associated with the stent component, said sleeve having a first end and a second end, wherein the sleeve is positioned parallel with the stent component, the composition of the sleeve being chosen from a group consisting of collagen, polytetrafluoroethylene, polyesters, polyurethane and silicones.

15. A sleeve carrying stent as in claim 14 wherein the struts are loosely interlocked to the stent component at a point generally equidistant from either end of the stent component.

16. A sleeve carrying stent as in claim 15 wherein the struts have securing means, the ends of the sleeve being secured in placed by the securing means, and wherein the length of the struts and the sleeve remain substantially constant during the radial expansion of the stent component.

17. A sleeve carrying stent as in claim 16 wherein the struts are radially spaced and have substantially the same length as the stent component in its collapsed form.

18. A sleeve carrying stent as in claim 17 wherein there are three struts.

19. A sleeve carrying stem as in claim 18 wherein the struts have radial perpendicular members extending from the ends of the struts, the members having a rounded configuration around the longitudinal axis of the strut.

20. A sleeve carrying stent as in claim 19 wherein the struts and the sleeve are on the same side of the stent wall.

21. A sleeve carrying stent as in claim 14 wherein the struts have securing means, the ends of the sleeve being secured in placed by the securing means, and wherein the length of the struts and the sleeve remain substantially constant during the radial expansion of the stent component.

22. A sleeve carrying stent as in claim 21 wherein the struts are radially spaced and have substantially the same length as the stent component in its collapsed form.

23. A sleeve carrying stent as in claim 22 wherein there are three struts.

24. A sleeve carrying stent as in claim 23 wherein the struts have radial perpendicular members extending from the ends of the struts, the members having a rounded configuration around the longitudinal axis of the strut.

25. A sleeve carrying stent as in claim 24 wherein the securing means are barbs positioned on the ends of the strut.

26. A sleeve carrying stent as in claim 24 wherein the struts and the sleeve are on the same side of the stent wall.

27. A sleeve carrying stent as in claim 24 wherein the sleeve is positioned on the opposite side of the stent wall than that of the struts.

28. A sleeve carrying stent as in claim 27 wherein the struts are on the outside of the stent wall.

29. A sleeve carrying stent as in claim 27 wherein the struts are on the inside of the stent wall.

30. A sleeve carrying stent for implantation within a body lumen comprising;

a radially expandable cylindrical stent component having a first open end and a second open end, an inner wall and an outer wall;

three elongated support struts, each of said struts having a first end, a second end, a longitudinal axis and securing means, said securing means comprising barbs positioned on the ends of said struts, said struts further being carried by the stent component and being loosely interlocked with the stent component at a point generally equidistant from either end of the stent component, said struts being radially spaced and having substantially the same length as the stent component in its collapsed form, said struts further having radial perpendicular members extending from the ends of the struts, said members having a rounded configuration around the longitudinal axis of the strut, and wherein the stent component is able to move longitudinally independent of the struts, and the length of the struts remains substantially constant during the radial expansion of the stent component; and a biocompatible open ended tubular sleeve associated with the stent component, said sleeve having a first end and a second end, the composition of said sleeve being selected from the group consisting of collagen, polytetrafluoroethylene, polyesters, polyurethane and silicones, and wherein the sleeve is positioned parallel with the stent component, the ends of said sleeve being secured in place by the barbs of the support struts, and the length of the sleeve remains substantially constant during the radial expansion of the stent component.

31. A sleeve carrying stent for implantation within a body lumen comprising:

a radially expandable cylindrical stent component having a first open end and a second open end, an inner wall and an outer wall;

three elongated support struts, each of said struts having a first end, a second end, a longitudinal axis and securing means, said struts further being carried by the stent component and being loosely interlocked with the stent component at a point generally equidistant from either end of the stent component, said struts being radially spaced and having substantially the same length as the stent component in its collapsed form, said struts further having radial perpendicular members extending from the ends of the struts, said members having a rounded configuration around the longitudinal axis of the strut, and wherein the stent component is able to move longitudinally independent of the struts and the length of the struts remains substantially constant during the radial expansion of the stent component; and a biocompatible open ended tubular sleeve associated with the stent component, said sleeve having a first end and a second end, the composition of said sleeve being selected from the group consisting of collagen, polytetrafluoroethylene, polyesters, polyurethane and silicones and wherein the sleeve is positioned parallel with the stent component and on the opposite side of the stent wall than that of the struts, the ends of said sleeve being secured in place by the securing means of the support struts, and the length of the sleeve remains substantially constant during the radial expansion of the stent component.

32. A sleeve carrying stent as in claim 31 wherein the struts are on the outside of the stent wall.

33. A sleeve carrying stent as in claim 31 wherein the struts are on the inside of the stent wall.

34. A sleeve carrying stent for implantation within a body lumen comprising:

a radially expandable cylindrical stent component having open ends, an inner wall and an outer wall;

three elongated support struts, each of said struts having a first end, a second end, a longitudinal axis, securing means comprising barbs positioned on the ends of the struts, and radial perpendicular members extending from the ends of the struts, the members having a rounded configuration around the longitudinal axis of the strut, said struts being carried by and parallel with the stent component, said struts being radially spaced and having substantially the same length as the stent component in its collapsed form, the length of said struts remaining substantially constant during the radial expansion of the stent component, and wherein the stent component is able to move longitudinally independent of the struts; and a biocompatible open ended tubular sleeve associated with the stent component, said sleeve having a first end and a second end, said sleeve being positioned parallel with the stent component and secured in place by the securing means of the struts, wherein the length of said sleeve remains substantially constant during radial expansion of the stent component, the composition of said sleeve being selected from the group consisting of collagen, polytetrafluoroethylene, polyesters, polyurethane and silicones.

35. A sleeve carrying stent as in claim 34 wherein the struts and the sleeve are on the same side of the stent wall.

36. A sleeve carrying stent for implantation within a body lumen comprising:

a radially expandable cylindrical stent component having open ends, an inner wall and an outer wall;

three elongated support struts, each of said struts having a first end, a second end, a longitudinal axis, securing means, and radial perpendicular members extending from the ends of the struts, the members having a rounded configuration around the longitudinal axis of the strut, said struts being carried by and parallel with the stent component, said struts being radially spaced and having substantially the same length as the stent component in its collapsed form, the length of said shuts remaining substantially constant during the radial expansion of the stent component, and wherein the stent component is able to move longitudinally independent of the struts; and a biocompatible open ended tubular sleeve associated with the stent component, said sleeve having a first end and a second end, said sleeve being positioned parallel with the stent component and secured in place by the securing means of the struts, said sleeve being positioned on the opposite side of the stent wall than that of the struts, wherein the length of said sleeve remains substantially constant during radial expansion of the stent component, the composition of said sleeve being selected from the group consisting of collagen, polytetrafluoroethylene, polyesters, polyurethane and silicones.

37. A sleeve carrying stent as in claim 36 wherein the struts are on the outside of the stent wall.

38. A sleeve carrying stent as in claim 36 wherein the struts are on the inside of the stent wall.

39. A sleeve carrying stent for implantation within a body lumen comprising:

a radially expandable cylindrical stent component having open ends, an inner wall and an outer wall;

a plurality of elongated support struts carried by the stent component, wherein the struts are parallel and loosely interlocked with the stent component, and wherein the stent component is able to move longitudinally independent of the struts; and an open ended tubular collagen sleeve associated with the stent component, wherein the sleeve is positioned parallel with the stent component, and is secured to the struts; said sleeve carrying stent being constructed and arranged for implantation and expansion with the sleeve and struts incorporated with the stent.

40. A sleeve carrying stent for implantation within a body lumen comprising:

a radially expandable cylindrical stent component having open ends, an inner wall and an outer wall;

a biocompatible open ended tubular sleeve, wherein the sleeve is positioned parallel with the stent component; and a plurality of elongated rod-shaped support struts incorporated in the sleeve, wherein the struts are parallel with the stem component, and wherein the stem component of the sleeve carrying stent is able to move longitudinally independent of the sleeve; said sleeve carrying stent being constructed and arranged for implantation and expansion with the sleeve and struts incorporated with the stent.

* * * * *